United States Patent [19]

Temin

[11] 4,188,317
[45] Feb. 12, 1980

[54] DENTAL RESTORATIVE COMPOSITIONS CONTAINING TITANIUM SILICATE

[75] Inventor: Samuel C. Temin, Needham, Mass.

[73] Assignee: Colgate-Palmolive Company, New York, N.Y.

[21] Appl. No.: 929,069

[22] Filed: Jul. 28, 1978

[51] Int. Cl.$^2$ ............................ C08K 3/24; C08K 3/34
[52] U.S. Cl. ............................... 260/42.53; 260/42.52; 260/998.11
[58] Field of Search .............. 260/42.53, 998.11, 42.52

[56] References Cited

U.S. PATENT DOCUMENTS 3,709,866  1/1973  Waller .............................. 260/998.11

Primary Examiner—Sandra M. Person
Attorney, Agent, or Firm—Norman Blumenkopf; Herbert S. Sylvester; Murray M. Grill

[57] ABSTRACT

Titanium silicate is used as the filler for dental restorative composites, especially dental restoratives cements, in combination with a conventional liquid polymerizable binder system, especially BIS-GMA combined with one or more dimethacrylates. The composite compositions possess improved mechanical properties, especially compressive strength, as well as a low coefficient of thermal expansion.

10 Claims, No Drawings

DENTAL RESTORATIVE COMPOSITIONS CONTAINING TITANIUM SILICATE

BACKGROUND OF THE INVENTION

1. Field of Invention

This invention relates to dental restorative composite compositions, and particularly, to the use of titanium silicate as the finely divided, inorganic filler in dental restorative composites.

2. Discussion of the Prior Art

Dental restorative composites, generally in the form of highly filled blends of a liquid polymerizable organic resin matrix and finely divided inorganic particulate filler, have achieved wide commercial success and are used extensively in clinical dental practice. Basically, most of the dental restorative composites which have become commercially available or which are described in the literature, are based upon the development of the system first disclosed by Bowen in U.S. Pat. No. 3,066,112.

In the direct filling system or restorative composite described by Bowen in this patent, the liquid polymerizable organic resin matrix or binder is principally the reaction product of bisphenol A and glycidyl methacrylate, referred to as BIS-GMA, preferably combined with one or more other active monomers, referred to as reactive diluents, especially other dimethacrylates, for example, triethylene glycol dimethacrylate. The system also includes a catalyst or polymerization initiator, such as, for example, benzoyl peroxide and preferably, also, to allow the polymerization to take place in a reasonable period of time, a polymerization accelerator or activator, such as, for example, N,N-dimethyl-p-toluidine. A particularly attractive combination of catalyst and accelerator is a hydroperoxide, more stable than benzoyl peroxide, and a substituted thiourea, less prone to cause coloration than an amine accelerator, as disclosed in U.S. Pat. No. 3,991,008. Other ingredients, such as stabilizers or UV-absorbents may also be present in association with the polymerizable constituents to increase shelf life and otherwise prevent degradation of the properties of the restorative composite composition. Still further, these restorative composite compositions may include various dyes or pigments to obtain various shades to conform to the color of the tooth structure with which the restorative composite material is being used.

The composite restorative materials are generally provided for commercial use as multi-package systems, most typically a two package system with the system described in U.S. Pat. No. 3,926,906 to Lee et al. being most typical. In these systems, the reactive monomers are generally provided in the form of a paste blended with the finely divided inert inorganic filler with the reactive diluent and/or catalyst and/or activator maintained separately from the polymerizable ingredients or reactive diluent.

The most commonly used inorganic filler materials are typically crystalline quartz or amorphous silica, although other materials, such as, for example, fused silica, crystalline silica, glass, fused alumina and the like, have also been disclosed. It is also common practice to treat the filler or the binder or both, with a coupling agent, such as γ-methacryloxypropyltrimethoxysilane, to enhance adhesion between the organic matrix binder and the inert inorganic filler particles.

Other fillers have also been suggested which have a negative coefficient of thermal expansion. For instance, U.S. Pat. No. 3,503,128 suggests the use of β-eucryptite, a lithium aluminum silicate. The use of fillers of low or negative coefficients of thermal expansion is highly desireable in order to more closely match the resultant composite with the tooth structure in terms of thermal expansion. In general, composite restorations which are highly loaded with the inorganic filler particles are more nearly compatible with tooth structure than the previously used unfilled resin restorative compositions. Thus, over the pertinent region of 0–60° C., tooth enamel has a coefficient of thermal expansion of about $11 \times 10^{-6}$ (or 11 ppm), whereas, an unfilled resin has a corresponding value of coefficient of thermal expansion of about 80–100 ppm.

However, restorative composites based on β-eucryptite and other fillers with negative or close to zero coefficients of thermal expansion are characterized by poor physical properties and particularly, low compressive strength.

OBJECTS AND SUMMARY OF INVENTION

It is accordingly an objective of the present invention to provide a dental restorative composition of the type comprising a blend of liquid polymerizable resin binder matrix and a finely divided solid inert inorganic filler which has a low coefficient of thermal expansion without any loss of essential physical properties, such as compressive strength.

It is a further object of the present invention to provide a dental restorative composition which is attractive in appearance, i.e. has an index of refraction and translucency comparable to natural tooth enamel.

It is still a further object of the present invention to provide such dental restorative composite which is easy to use and handle by a dentist.

These and other objects of the present invention will become more apparent from the following detailed description and are provided by employing titanium silicate as the finely divided inert inorganic filler. It has now been found that dental restorative composite compositions employing titanium silicate as the filler have low coefficients of thermal expansion, excellent translucency, low thermal conductivity and enhanced compressive strength.

The polymerixable organic binder can be any of the type conventionally used in dental restorative composites, expecially those based upon BIS-GMA and other multi-functional methacrylates along with the conventional initiators or catalysts and optionally, accelerator compounds. In addition, pigments, UV absorbers and stabilizers, as well as other inert inorganic finely divided filler particles can also be present in the composite compositions.

DETAILED DESCRIPTION AND PREFERRED EMBODIMENTS

Titanium silicate, also described as "titanium-doped silica", has the chemical formula:

$$(SiO_2)_x (TiO_2)_y$$

where $x = 92.5$ to 95 and $y = 5$ to 7.5 The titanium content is between about 4 to 6% by weight, preferably about 5% by weight. This corresponds to values of x and y of about 93.8 and 6.2, respectively. Titanium silicate is produced by condensation from a vapor form by flame hydrolysis and can be purchased from Corning Glass Works as Corning #7971 ULE.

Titanium silicate is commercially available in the form of large shaped objects or as cullets (large pieces) produced in the process of cutting the bulk object to final shape. For use in the dental restorative composites of this invention, it is necessary to grind the titanium silicate cullets to the desired average particle size. This is easily accomplished by any conventional grinding means, such as, for example, a ball-mill.

The thermal expansion coefficient of titanium silicate is essentially zero over the temperature range of 0 to 60° C., preferably 0 to 100° C.

The titanium silicate is also characterized by a Knoop hardness of about 459 Kg/mm$^2$ at 200 gram load which is greater than that of borosilicate glass, a density of about 2.2 g/cm$^2$, an index refraction of about 1.48 and a thermal conductivity of about 0.00313 cal/cm. sec° C. This density is lower than that of quartz or silica and accordingly, less weight of the filler is required to obtain a given volume fraction of filler.

Preferably, the titanium silicate has a particle size distribution ranging from submicron to not more than about 10 microns. Preferably, the titanium silicate is ground to a mean particle size of from about 1.1 microns to 3.5 microns, most preferably, between 1.1 and 1.5 microns, as determined by a sedigraphic particle size distribution measurement.

The titanium silicate filler is present as as least the major proportion of the total amount of filler and preferably, constitutes from about 65 to 100% of the total amount of filler and most preferably, at least about 70 to 100% of the total filler. Generally, the filler conistutes from about 50% by weight to about 90% by weight of the total composite, and preferably, about 65 to 85% by weight of the total composite composition.

Any of the other conventional fillers can be present in minor amounts based upon the total weight of filler. Representative of such suitable materials are silica, glass beads, aluminum oxide, fused silica, fused or crystalline quartz, and the like. The particle size of the additional materials generally range from submicron to about 125 microns with the average particles size being in the range of from about 1 to 20 microns and preferably, from about 2 to about 5 microns. A mixed filler containing about 60-80 parts by weight titanium silica and about 40-20 parts by weight amorphous silica impart especially high compressive strength to the resulting composite. Also, while the titanium silicate filled dental restorative composites of this invention possess greater x-ray opacity than composites utilizing conventional siliceous fillers, it may be desired to incorporate minor amounts of x-ray opaque glass or other x-ray absorbing elements with the titanium silicate filler.

Any of the conventionally available liquid polymerizable organic resin binder systems including polymerizable monomers, reactive diluents, catalysts, accelerators, UV absorbers, pigments and the like, can be used satisfactorily in this invention. The preferred polymerizable monomers are those based upon BIS-GMA and other di-, tri- and tetra-methacrylates, and particularly, the binder system, as disclosed by Bowen in the aforementioned U.S. Pat. No. 3,066,112. Other suitable polymerizable monomer systems are disclosed, for example, in U.S. Pat. Nos. 3,179,623, 3,539,533, 3,730,947, 3,751,399, 3,766,132, 3,774,305, 3,835,090, 3,839,065, 3,845,009, 3,853,962, 3,860,556, 3,862,920, 3,882,600, 3,911,581, 3,923,740 and 3,928,280.

Each of these patents teach polymerizable monomer systems, along with suitable catalysts and accelerators and other conventionally used adjuvants and additives in dental restorative composite compositions. The disclosures of these references should therefor be considered to be incorporated herein by reference. Reference is also made to the patent to Temin et al., U.S. Pat. No. 3,991,008, for the description of a redox catalyst system which can be used in the present invention.

In addition to the foregoing components of the composite compositions, it is also preferred to utilize a coupling agent for enhancing the adhesion of the inert inorganic filler particles with the binder matrix. For this purpose, it is conventional in the art to use ethylenically unsaturated organo silane compounds such as γ-methacryloxypropyltrimethoxysilane, vinyl trichlorosilane, vinyl triethyoxysilane, vinyl trimethoxysilane, vinyl triacetoxysilane, and the like. The coupling or keying agent can be added to the filler material prior to blending the filler and liquid polymerizable matrix or it can be added to the liquid matrix prior to incorporation therein of the filler particles.

Generally, the filler and binder are combined in proportions of about 1:1 to about 6:1, preferably about 2:1 to about 5:1.

The catalyst and optional activator are each generally employed in amounts from 0.1 to 1.0% by weight based on the weight of active monomer or monomers present. However, higher or lower amounts depending upon the monomers and types of catalysts or activator can be used.

As with the conventional dental restorative composite compositions, the compositions of this invention may conveniently be provided to the dentist in the so-called two package system, such as described in U.S. Pat. No. 3,926,906. According to the packaging system described in this patent, each package contains the unpolymerized monomers and any reactive diluents and inorganic filler, preferably in the proportion present in the final product. One package contains the initiator or catalyst and the other package contains the reductant or accelerator. By combining roughly equal portions from the two packages, the catalyst and accelerator in each react to generate free radicals, thereby causing polymerization of the polymerizable resin system.

Each of these patents teach suitable polymerizable monomers, reactive diluents, catalysts, accelerators and other conventionally used adjuvants and additives in dental restorative composite compositions for such applications and dental fillings, dental cements and the like. Accordingly, the disclosures of these references should therefor be considered to be incorporated herein by reference.

The use of the particulate titanium silicate filler according to this invention has the following advantages aver the typical fillers conventionally used, such as, quartz or the various types of silica. These advantages include, for example, the excellent aesthetic properties of the composites and their ability to be pigmented to desirable tooth matching shades. The composites have a translucency similar to human tooth in appearance and are more attractive to the eye. The titanium silicate fillers do not require any laborious cleaning procedure, whereas other fillers generally require an acid wash to remove deleterious cations. The thermal expansion coefficient of the composites of this invention will closely approximate that of tooth structure, while providing high compressive strengths, approaching the values of healthy tooth structure being achieved. Also, the composites of this invention utilizing titanium silicate filler have a lower coefficient of thermal conductivity, thereby reducing likelihood of thermal sensitivity and pupal injury due to heat transfer through the restoration. Also, the titanium silicate fillers have high Knoop hardness and a relatively low density thereby requiring a lesser weight of filler to obtain a given volume fraction of filler.

This invention will now be described by the following illustrative and non-limiting examples.

EXAMPLE 1

A sample of titanium silicate sold by the Corning Glass Works, Corning, New York, as "No. 7971 ULE" was ball-milled to a mean particle size of 3.2 microns. This titanium silicate product is described by Corning Glass Works as a synthetic amorphous silica glass with a thermal expansion coefficient which is essentially zero over a temperature range of 0 to 60° C. A second sample was prepared from the same titanium silicate cullet by further ball-milling to a mean particle size of 1.3 microns. In both cases, measurements of the particle size were obtained by Sedigraph measurements.

Dental restorative composites were prepared by combining 75% by weight of the titanium silicate filler with a liquid phase binder having a 1:1 by weight mixture of BIS-GMA and hexamethylenedimethacrylate. The liquid binder phase additionally contained 5% by weight, based on the total monomers, of $\gamma$-methacryloxypropyltrimethoxy silane, a coupling agent, and 1% by weight based on the total monomers of acetylthiourea, the reductant portion of the redox initiator.

To portions of each of the resulting pastes cumene hydroxide was added in an amount equivalent to 2% by weight of the monomers. The mixture was well spatulated and then placed in a cylindrical mold. The cured composites were then evaluated for compressive strength with the results being shown in the following table.

TABLE
EFFECT OF TITANIUM SILICATE PARTICLE SIZE ON COMPRESSIVE STRENGTH

| Sample | Mean Size of Titanium Silicate (Micron) | Compressive Strength (psi) |
| --- | --- | --- |
| 1 | 3.2 | 39,100 ± |
| 2 | 1.3 | 47,400 ± 9,500 |

A composite similar to that of Sample 2 was prepared, except that 25% of the titanium silicate filler was replaced by the same weight of 2.3 micron average particle size silica. The composite with the mixed filler gave a compressive strength value of 48,000±3,600 psi.

COMPARATIVE EXAMPLE 1

Using the identical resin phase as in Example 1, a composite was prepared utilizing 76% by weight of an amorphous silica. Cylinders of the cured composite were tested to determine the coefficient of thermal expansion using a thermomechanical analyzer. The coefficient of thermal expansion over the range 0–60° C. was 39.4 ppm for the composite containing the amorphous silica filler. In contrast, the coefficient of thermal expansion for the composite of Example 1 was 30.4 ppm.

What is claimed is:

1. In a dental restorative composite composition, which is a mixture of a finely divided, inert inorganic filler and a liquid polymerizable resin binder system, the improvement comprising, as at least the major portion of said finely divided inert inorganic filler, titanium silicate.

2. The composite of claim 1, wherein the titanium silicate filler has an average particle size in the range of from less than about 1 micron up to about 10 microns.

3. The composite of claim 1, wherein the titanium silicate filler has an average particle size in the range of from about 1.1 microns to about 3.5 microns.

4. The composite of claim 1, wherein the finely divided, inert inorganic filler comprises at least 65% by weight of titanium silicate.

5. The composite of claim 1, wherein the finely divided, inert inorganic filler consists solely of titanium silicate.

6. The composite of claim 1, wherein the ratio of filler to binder is from about 1:1 to about 6:1 by weight.

7. The composition of claim 1 wherein the resin binder system includes the reaction product of bisphenol A and glycidyl methacrylate.

8. The composition of claim 7 wherein the resin binder further contains hexamethylene dimethacrylate.

9. The composition of claim 7 wherein the inorganic filler comprises at least 65% by weight of titanium silicate of an average particle size of from less than about 1 micron up to about 10 microns.

10. The composition of claim 9 which further contains a methacrylate selected from the group consisting of di-, tri, and tetra-methacrylates and mixtures thereof.

* * * * *